United States Patent [19]

Dean et al.

[11] Patent Number: 4,923,455
[45] Date of Patent: May 8, 1990

[54] DISPOSABLE DIAPER WITH INTEGRAL DISPOSAL ENVELOPE

[75] Inventors: Raymond S. Dean, Lynn; William A. Barabino, North Reading, both of Mass.

[73] Assignee: Personal Hygiene Research Associates, North Reading, Mass.

[21] Appl. No.: 190,088

[22] Filed: May 4, 1988

[51] Int. Cl.⁵ .............................................. A61F 13/16
[52] U.S. Cl. .................................. 604/385.1; 604/389
[58] Field of Search ............................. 604/385.1, 389

[56] References Cited

U.S. PATENT DOCUMENTS

| 3,920,019 | 11/1975 | Schaar | 604/385.1 |
| 3,927,674 | 12/1975 | Schaar | 604/385.1 |
| 4,430,087 | 2/1984 | Azipiri | 604/385.1 |
| 4,540,415 | 9/1985 | Korpman | 604/390 |
| 4,551,145 | 11/1985 | Ryan | 604/389 |
| 4,581,027 | 4/1986 | Alvarado | 604/385.1 |
| 4,604,096 | 8/1986 | Dean et al. | 604/385.2 |
| 4,808,175 | 2/1989 | Hansen | 604/385.1 |

Primary Examiner—C. Fred Rosenbaum
Assistant Examiner—Mark O. Polutta
Attorney, Agent, or Firm—Richard C. Litman

[57] ABSTRACT

A disposable diaper includes a sealable disposal envelope integrally attached along a belt area seam of the diaper. A sealing tape-belt member adhered to the envelope provides an airtight seal of this envelope when the used diaper is folded and then inturned around the seam and placed within the envelope. The seam is adherently formed, by among other possibilities, by a heat seal or adhesive such as a double stick adhesive tape. The sealing tape is also provided with an adhesive on both faces. One face of the sealing adhesive is attached to the inside of the envelope while the other face performs a dual function. Initially, this other face secures the opening of the un-used disposal bag in a closed manner but subsequently serves to sealingly close this bag opening following infolding of the used diaper into the attached disposal bag. During use of the diaper, the sealing tape operates as a belt, permitting form-fitting of the diaper about the body. In one embodiment, the belt area of the diaper has two slits and the tape ends extend through these slits. Protective strips on the double stick adhesive of the tape cover portions of the adhesive until ready for usage. With this arrangement, refastenable tabs are provided to allow form-fitting of the diaper during its use and additionally, adjacent adhesive portions are exposable after the diaper has been used, to permit the sealing of the disposal bag following insertion of the used diaper therewithin.

4 Claims, 2 Drawing Sheets

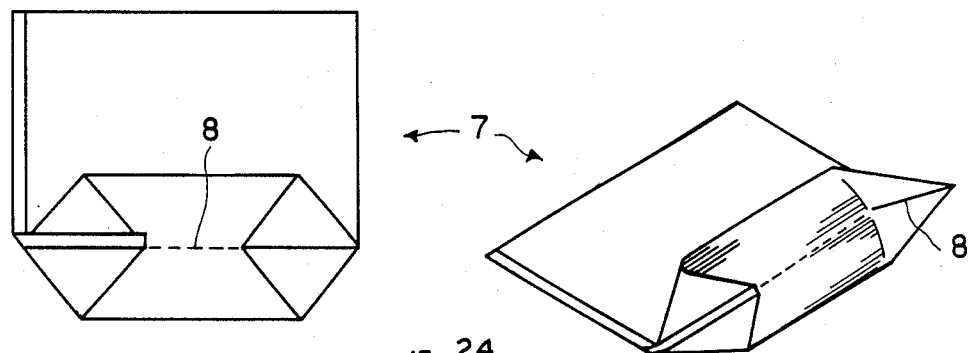
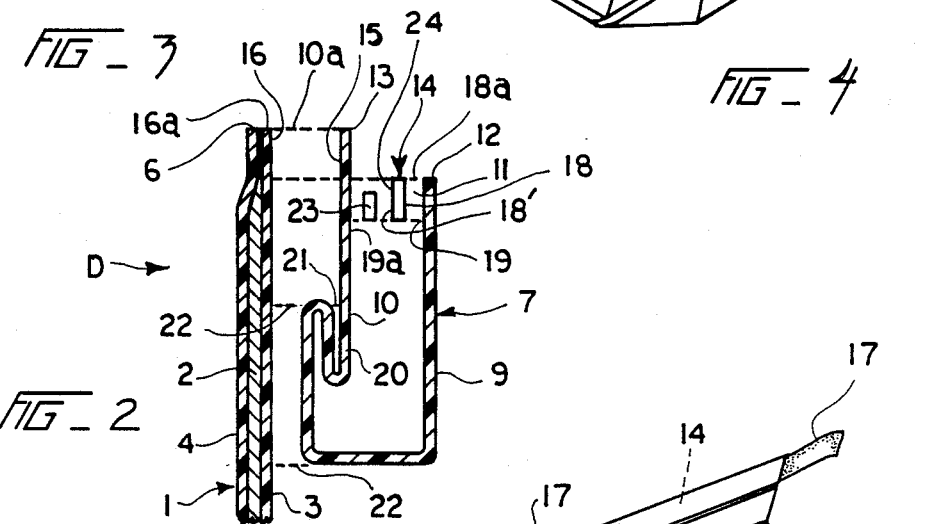
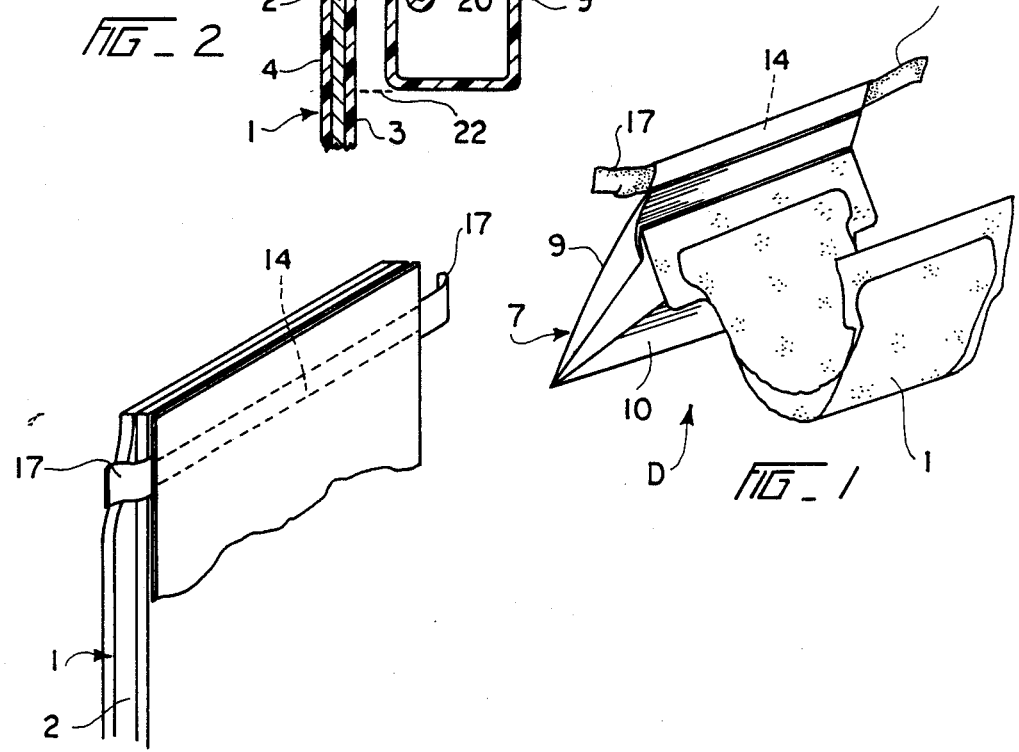

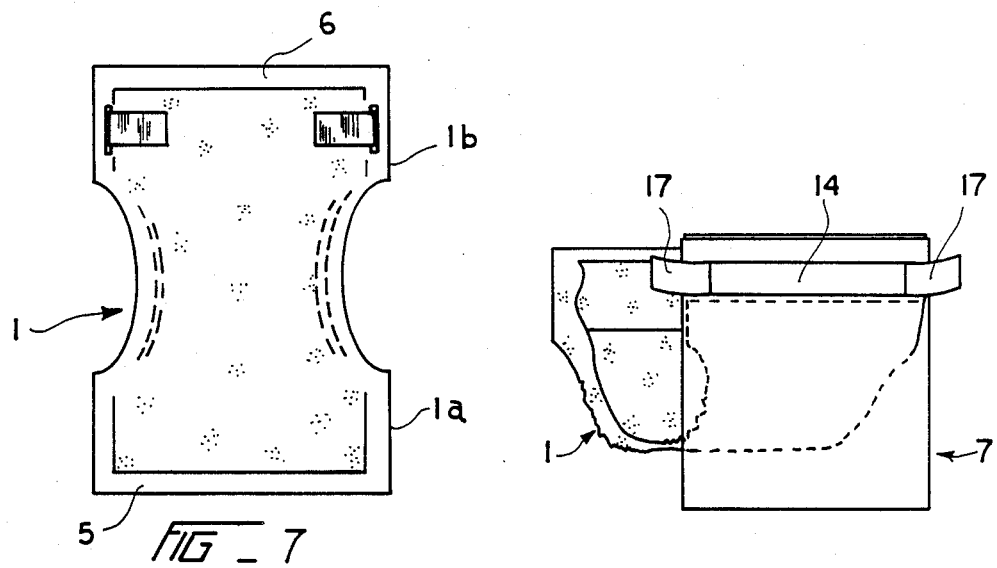
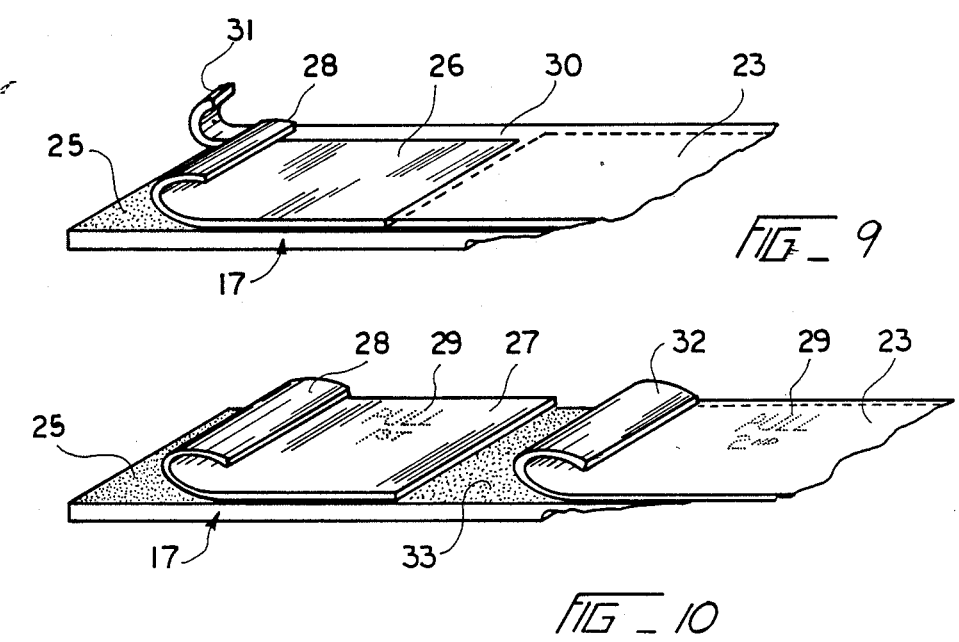

DISPOSABLE DIAPER WITH INTEGRAL DISPOSAL ENVELOPE

BACKGROUND OF THE INVENTION

Considerate disposal of diapers poses an unsolved problem particularly as far as disposable diapers associated with an integrally attached sealed envelope is concerned. There are presently no effective integral sealing means to insure the airtightness of such a disposable envelope, following the containment of the used diaper.

Improvements relating to disposable diapers have been directed primarily to the areas of absorbency, softness and elastic form fitting features around the legs, as well as the means for securing the diaper in its use position, about the waist of the inant. There are no known successful efforts at providing an integral means for insuring the sealing of an attached disposal envelope, to preclude the passage or leakage of fluids which, in addition to being effective, also meets with complete satisfaction of the attending party.

Without an adequate sealing of the disposal envelope, the formation of disagreeable odors will obviously be of paramount concern and presents a problem that must be addressed.

DESCRIPTION OF THE RELATED ART

U.S. Pat. No. 4,604,096 to applicant in Dean, et al., is drawn to an integral envelope and diaper with adhesive means mounted proximate a free end for securing shut the mouth of the envelope for disposal of the used diaper. It does not have a double stick adhesive tape at the opening of the mouth to make a complete airtight seal of the opening.

U.S. Pat. No. 4,430,087 to Azpiri calls for a disposable diaper with an open end in the layers of the diaper for placement of the disposal envelope. Again, there is no provision to obtain a complete airtight seal of the envelope when the used diaper has been disposed of in the envelope.

U.S. Pat. No. 3,274,999 to Robinson is drawn to an integral anatomical dressing covering fabric sheet and is unlike the present invention which retains the envelope to the belt area of the diaper exteriorly of the diaper, but integral therewith.

U.S. Pat. No. 3,369,545 to Wanberg relates to a disposable diaper having a pouch but wherein the diaper forms a part of the pouch, unlike the present invention wherein the envelope while being integrally attached to the diaper is, however, attached to the the diaper along a seam.

U.S. Pat. No. 3,585,999 to Wanberg is drawn to an integral disposal envelope and diaper but there is no apparent means for ensuring an airtight seal of the envelope after the used diaper is enclosed therein.

U.S. Pat. No. 4,685,916 to Encloe relates to a disposable garment having an elastic waist as does also, U.S. Pat. No. 4,681,580 to Reising, et al.

SUMMARY OF THE INVENTION

The present invention is drawn to a sealable disposal envelope integrally attached adjacent a belt area seam of a disposable diaper. Included is a combination sealing tape-belt member serving initially to provide a form-fitting back belt to retain the diaper in its use position and thereafter, operable as a fastening and sealing mechanism to provide an airtight seal of the attached disposal envelope when the used diaper is infolded into the envelope. The seal is adherently formed by among other possibilities, an adhesive such as a double stick adhesive tape. The sealing tape-belt member thus may comprise an adhesive tape with permanent adhesive on both faces. One face of the adhesive is attached to the inside of the envelope adjacent its opening while the other face is adapted initially to retain the envelope in a closed condition and thereafter to provide a sealing of the opening of the envelope following the infolding of the attached soiled diaper therein. In one embodiment the rear of the diaper to which the tape-belt member is affixed is provided with slits and the tape ends extend through these slits.

BRIEF DESCRIPTION OF THE DRAWINGS

FIG. 1 is a top perspective view of an integral diaper and disposal envelope according to the present invention, shown during the disposal operation and wherein, the sealing adhesive tape-belt member is poised for the diaper to be inserted into the opening of the envelope;

FIG. 2 is a partial, vertical sectional view illustrating a preferred manner of securing the integral, folded envelope in its storage position behind the diaper;

FIGS. 3 and 4 illustrate the folding of the end of the envelope prior to its attachment behind the diaper;

FIG. 5 is a partial rear perspective view of the diaper as it is readied to be attached to the front of the diaper during application upon an infant;

FIG. 6 is a rear perspective view of the diaper assembly shown in FIG. 1;

FIG. 7 is a plan view of the absorbent inner layer of the diaper and wherein a pair of slits are provided adjacent the ends of the tape-belt member;

FIG. 8 is a view similar to FIG. 13, of an alternate embodiment; and

FIGS. 9 and 10 are fragmentary perspective views of alternate embodiments of the end tabs of the double stick adhesive tape-belt member as shown before use of the diaper.

Similar reference characters designate corresponding elements throughout the several figures of the drawings.

DETAILED DESCRIPTION OF THE PREFERRED EMBODIMENTS

Referring now to the drawings, particularly FIGS. 1 and 2, the present invention will be seen to relate to a disposable diaper assembly, generally designated D and which includes a diaper 1 of the disposable type comprising well known elements forming a front 1a and back 1b portion including an inner absorbent material layer 2 bounded by an outer liner 3 on the one side an an inner liner 4 on the other. As is typical with such a diaper, the outer liner 3 is liquid impervious while the inner liner 4 readily admits of passage of liquid as received from an infant juxtapose this liner but discourages the reverse passage of liquid as absorbed by the adjacent or intermediate material layer 2. In the use of this diaper 1, one end having a terminal edge 5 will be designanted the front edge or portion and will be adapted to be disposed adjacent the front or stomach of the infant while the opposite end includes a terminal edge 6 comprising a rear edge intended to be disposed adjacent the rear or back of the infant.

The diaper assembly 1 includes the combination of a unique disposal envelope 7, shown alone in FIGS. 3-4 and in its usual attached relationship with the diaper 1, in FIGS. 1 and 2. This envelope 7 comprises any suitable lightweight, impervious material having a closed bottom or end 8 formed by an outer panel 9 and an inner panel 10. As shown most clearly in FIG. 2, these panels define an envelope opening 11 between the outer panel terminal edge 12 and the adjacent inner panel terminal edge 13.

An important feature of the present invention involves the manner of attachment of the disposal envelope 7 to the back or rear of the diaper 1, by means of a combination tape-belt member 14 that serves the dual role of providing a manner of attaching the envelope to the rear of the diaper in a storage position as the diaper is being worn and which includes unique structure allowing of subsequent utilization of this same member to provide a secure sealing of the envelope opening 11 following infolding of the soiled diaper 1 therein. Additionally, during use of the diaper, this same tape-belt member 14 operates as a back belt with fastening tabs to secure the rear of the diaper to its front portion when enveloped about the infant.

The diaper assembly D is originally manufactured with the disposal envelope 7 permanently affixed to the rear of the diaper as shown most clearly in the exploded view of FIG. 2. It will be appreciated that the envelope closed end 8 may be appropriately tucked or folded as shown in FIGS. 3-4 to minimize its size and obviousness as finally assembled with the diaper 1. The fixation of the envelope 7 to the diaper outer liner 3 is achieved by any suitable means such as a permanent adhesive 10a, bonding the forward face 15 of the inner panel 10, immediately adjacent its edge 13, to the outside face 16 of the diaper outer liner 3, adjacent its rear terminal edge 16a. As thus affixed, the two attached edges 13 and 16a will be seen to be flushly disposed.

As the diaper assembly D is manufactured and initially used, the envelope opening 11 will be understood to be closed and this is accomplished by means of the tape-belt member 14, comprising an elongated strip of flexible material having a length greater than the width of both the envelope 7 and diaper 1, and which terminates in a pair of laterally projecting end tab portions 17—17. An outer surface 18 of the belt member 14 is permanently affixed to the inner surface 19 of the envelope outer panel 9, immediately adjacent its edge 12, as at 18a with the two tab portions 17—17 projecting laterally therefrom. With this arrangement, the tape-belt member 14 may be used as a back belt to snugly retain the diaper 1 upon an infant, with the two tab portions 17—17 cooperating with the front of the diaper as will be described hereinafter.

The vertical extent of the stored envelope is reduced, not only to minimize its obviousness but also to eliminate its presence adjacent the wearer's buttocks. Accordingly, it will be seen that the lower portion of the envelope 7 is double-folded as at 20 and its retention in this configuration is assured, during wear of the diaper, by means of a plurality of tack points 21 between the upwardly folded portion and the adjacent inner panel 10 as well as by similar tack points 22 along opposite ends of the folded portion adjacent the diaper outer liner 3. These tack points 21-22 may comprise any well known means such as by heat searing or adhesive spots, so that one may fully extend the envelope 7 from the storage position of FIG. 2 to the disposal position of FIG. 1, simply by pulling the double-folded envelope 7 away from the rear of the diaper outer liner 3.

In the storage position, the disposal envelope 7 is retained in a closed condition and its outer panel 9 attached to the diaper outer liner 3 by the same tape-belt member 14. This is achieved by a pressure sensitive adhesive coating on the entire inner surface 18' thereof. However, as shown in FIG. 2 of the drawings, a central protective strip 23 overlies the majority of the width of the belt member 14, leaving an uppermost central exposed belt adhesive area 24. This latter adhesive area 24 provides the attachment means to retain the envelope closed, adjacent its edges 12-13, and the diaper outer liner 3 as the adhesive area 24 engages the inner surface 19a of the inner panel 10.

With the above construction in mind, it will be appreciated that during attachment and wearing of the diaper 1, the belt member 14 will be employed to stretch the rear portion of the diaper above the buttocks of the infant while that portion of the tape-belt member intermediate the end portions 17—17 maintains the envelope opening 11 closed and retains the envelope affixed to the back of the diaper. The end tab portions 17—17 are specifically arranged to enable their functioning both during wearing of the diaper, as well as subsequently, during the infolding of the soiled diaper within the disposal envelope 7. As previously described, the inner surface 18' of the tape-belt member 4 that is juxtaposed the envelope inner panel 10, is provided with a suitable adhesive coating of the pressure sensitive type and this coating is initially covered, between the lateral confines of the envelope width, by the protective strip 23 which leaves exposed the adhesive area 24 serving to temporarily retain the envelope outer panel 9 affixed in a closed manner. FIGS. 9-10 depict a typical construction of the distal or tab portions 17—17 of the tape belt member 14. It will be understood that the adhesive coating on the inner surface 18' of the member 14 is of the refastenable type, that is, it permits re-use without noticeable loss of its fastening capability. Additionally, this adhesive coating extends to the very ends of the member 14, such that the tab portions 17—17 likewise are provided with this coating. To preclude pre-mature, unwanted sticking of the exposed tab portions 17—17 prior to use of the diaper assembly D, the inner surface of these portions are provided with suitable selectively removable protective strips as shown in FIGS. 9 and 10 of the drawings.

To expose the adhesive coating 25 at the end of the tab portions 17—17, so as to apply the diaper 1 to an infant, the user removes the protective strips 26 or 27, whereafter the exposed adhesive area 25 will be available to provide fastening of the tab portions 17—17 to the front of the diaper 1 after it is wrapped about the infant. To facilitate removal of either protective strip 26, 27, appropriate pull-tab means 28 may be provided at the outer end thereof, offering convenient finger-grasping means. This latter means may be formed by either end-folding the strips over themselves or, by forming the strips of a greater length so as to extend beyond the ends of the tape-belt end portions 17, 17. Additionally, suitable indicia 29 may be applied to the protective strips, offering instructions applicable to the function and/or sequence of removal thereof.

In the case of the embodiment of FIG. 9, the strip 26 will be seen to have a width less than that of the underlying tape-belt tab 17 and the remaining width is covered by another protective strip which is actually an integral extension 30 of the strip 23 while, in the arrangement of FIG. 10, the endmost strip 27 covers the full width of the underlying tab portion 17. In either instance, at least the majority of the width of the adhesive coating 25 will be seen to be exposed when the strip 26 or 27 is removed, so as to permit a positive fastening of the tape-belt member 14 to the front of the diaper 1 when applied about an infant.

When the diaper is soiled and it is removed from the infant by releasing the tab portions 17—17 from the diaper front, the disposal envelope is readied for reception of the folded diaper. This is accomplished by initially breaking loose the tack points 21–22 which until this time have retained the lower portion of the envelope 7 in its tucked and folded condition adjacent the back of the diaper outer liner 3. The diaper assembly will then appear as in FIG. 6, with the envelope 7 fully extended. Thereafter, the envelope outer panel 9 is pulled away from its inner panel 10, thus separating the relatively narrow adhesive area 24 of the back belt member 14 from its attachment to the inner panel 10 and allowing the envelope opening 11 to be expanded such as depicted in FIG. 1 of the drawings. At this time, continued folding of the diaper 1 upon itself is followed by infolding of the diaper into the opened disposal envelope 7. Final enclosure of the soiled diaper within the envelope is then obtained by removal of the back belt protective strip 23 either, by grasping the pull-tab 31 of the extension 30 (FIG. 9) or the pull-tab 32 of the main portion of the strip 23 (FIG. 10). The thus exposed adhesive coating 33, along with the previously exposed endmost adhesive coatings 25 will be seen to provide closure and sealing means extending the full length of the tape-belt member 14 and will become engaged with the inside face 15 of the integral envelope inner panel 10 after the soiled, folded diaper 1 is infolded within the envelope 7, thereby providing a complete air and fluid-tight packaging of the used diaper.

We claim:

1. The combination comprising;

a disposable diaper having a disposable envelope attached thereto, said diaper having opposite front and back portions provided with outer and inner liners having end terminal edges, said disposal envelope including an inner panel and outer panel each having an inner surface and provided with terminal edges defining an opening therebetween, said envelope inner panel having an inside face juxtaposed said diaper outer liner adjacent said diaper back portion terminal edge, means permanently affixing said envelope inner panel inside face to said juxtaposed diaper outer liner throughout substantially the entire width of said inner panel inside face, a tape-belt member having outer and inner surfaces, the majority of one said member surface permanently attached to one said envelope panel inner surface adjacent its respective said panel terminal edge, an exposed resealable adhesive layer portion on the other one said tape-belt member surface extending the width of said envelope to provide releasable attachment means for one said envelope panel relative the other said envelope panel inner surface to provide temporary closure means for said envelope opening, a removable protective strip initially overlying a substanial portion of said tape-belt member resealable adhesive layer adjacent said exposed portion thereof to allow only the remaining exposed portion thereof to provide said temporary closure of said envelope opening, end tab portions on said tape-belt member extending laterally from said envelope adjacent said diaper back portion, said resealable adhesive layer on said tape-belt member extending throughout said end tab portions to provide releasable fastening means thereon, said releasable attachment means operable to allow opening of said envelope opening as said exposed resealable adhesive layer portion is released from engagement with said other said envelope panel inner surface, said protective strip thereafter removable to fully expose the entire said resealable adhesive layer on said tape-belt member within said envelope, whereupon said diaper may be infolded into said permanently affixed envelope following which the full extent of said resealable adhesive layer on said tape-belt within said envelope is engageable with said other said envelope panel to fully encapsulate the infolded diaper within said envelope.

2. The combination according to claim 1 wherein, said disposal envelope includes a closed bottom, said closed bottom initially folded between said inner panel and said diaper outer liner, and means releasable connecting portions of said folded envelope to said diaper outer liner, whereby said releasable connecting means are separable to allow unfolding of said envelope prior to infolding of said diaper thereinto.

3. The combination according to claim 1 wherein, said envelope outer panel terminal edge is vertically spaced from said inner panel terminal edge.

4. The combination according to claim 1 including, a removable protective strip initially overlying said resealable adhesive layer on said end tab portions.

* * * * *